US010942166B2

(12) United States Patent
Cafferty

(10) Patent No.: US 10,942,166 B2
(45) Date of Patent: Mar. 9, 2021

(54) WHOLE BLOOD SO₂ SENSOR

(71) Applicant: Nova Biomedical Corporation, Waltham, MA (US)

(72) Inventor: Michael Cafferty, Medford, MA (US)

(73) Assignee: Nova Biomedical Corporation, Waltham, NH (US)

(*) Notice: Subject to any disclaimer, the term of this patent is extended or adjusted under 35 U.S.C. 154(b) by 0 days.

(21) Appl. No.: 16/097,448

(22) PCT Filed: May 11, 2016

(86) PCT No.: PCT/US2016/027243
§ 371 (c)(1),
(2) Date: Oct. 29, 2018

(87) PCT Pub. No.: WO2017/196290
PCT Pub. Date: Nov. 16, 2017

(65) Prior Publication Data
US 2019/0154660 A1 May 23, 2019

(51) Int. Cl.
G01N 33/49 (2006.01)
G01N 21/25 (2006.01)
(Continued)

(52) U.S. Cl.
CPC ..... *G01N 33/4925* (2013.01); *A61B 5/14551* (2013.01); *G01N 21/255* (2013.01);
(Continued)

(58) Field of Classification Search
CPC ............ G01N 33/4925; G01N 21/255; G01N 21/3151; G01N 21/3577;
(Continued)

(56) References Cited

U.S. PATENT DOCUMENTS 3,647,299 A 3/1972 Lavallee
5,267,562 A * 12/1993 Ukawa ............... A61B 5/14551
356/41

(Continued)

FOREIGN PATENT DOCUMENTS

CN 201556835 A 8/2010
CN 201556835 U 8/2010
(Continued)

OTHER PUBLICATIONS

K-OPLS package: kernel-based orthogonal projections to latent structures for prediction and interpretation in feature space, BMC Bioinformatics. 2008; 9:106. Published Feb. 19, 2008 by Max Bylesjö et al. (Year: 2008).*

(Continued)

*Primary Examiner* — Jamil Ahmed
(74) *Attorney, Agent, or Firm* — Robert R. Deleault, Esq.; Mesmer & Deleault, PLLC

(57) ABSTRACT

An oximeter sensor system includes a light source group having a plurality of LEDs including at least a first visible light LED, a second visible light LED and an infrared LED adjacent the first visible light LED and the second visible light LED, an infrared filter disposed in front of only the first visible light LED and the second visible light LED, a light source housing having a base, one or more sidewalls and a light-emitting end where the light source housing has a frustum shape where the light source group is disposed adjacent the base and facing the light-emitting end and where the one or more sidewalls has a reflective coating thereon, a light detector disposed opposite to, spaced from and facing the light-emitting end of the light source housing, and a cuvette disposed between the light-emitting end of the light source housing and the light detector.

19 Claims, 7 Drawing Sheets

(51) Int. Cl.
*G01N 21/3577* (2014.01)
*G01N 21/31* (2006.01)
*A61B 5/1455* (2006.01)

(52) U.S. Cl.
CPC ..... *G01N 21/3151* (2013.01); *G01N 21/3577* (2013.01); *G01N 2021/3144* (2013.01); *G01N 2021/3155* (2013.01); *G01N 2201/0627* (2013.01); *G01N 2201/0634* (2013.01); *G01N 2201/0636* (2013.01); *G01N 2201/12* (2013.01)

(58) Field of Classification Search
CPC ... G01N 2021/3144; G01N 2021/3155; G01N 2201/0627; G01N 2201/0634; G01N 2201/0636; G01N 2201/12; A61B 5/14551
See application file for complete search history.

(56) References Cited

U.S. PATENT DOCUMENTS

| | | | |
|---|---|---|---|
| 5,389,549 A | 2/1995 | Hamaguchi et al. | |
| 5,416,026 A | 5/1995 | Davis | |
| 6,615,064 B1* | 9/2003 | Aldrich | A61B 5/14532 600/316 |
| 6,623,972 B2 | 9/2003 | Malin et al. | |
| 7,671,974 B2 | 3/2010 | O'Mahony et al. | |
| 8,421,484 B2 | 4/2013 | Prodan et al. | |
| 8,478,546 B2 | 7/2013 | Katsumoto et al. | |
| 2002/0041371 A1 | 4/2002 | Shepherd et al. | |
| 2002/0110496 A1 | 8/2002 | Samsoondar | |
| 2004/0176670 A1 | 9/2004 | Takamura et al. | |
| 2005/0037505 A1 | 2/2005 | Samsoondar | |
| 2005/0094127 A1* | 5/2005 | O'mahony | A61B 5/14557 356/39 |
| 2010/0184120 A1 | 7/2010 | Tarasev et al. | |
| 2013/0094179 A1* | 4/2013 | Dai | F21V 9/30 362/84 |
| 2014/0093948 A1 | 4/2014 | Durrer et al. | |
| 2015/0109608 A1 | 4/2015 | Kim et al. | |

FOREIGN PATENT DOCUMENTS

| | | |
|---|---|---|
| GB | 1282919 | 7/1972 |
| JP | 2004517300 A | 6/2004 |
| JP | 2004230000 A | 8/2004 |
| JP | 2010521266 A | 6/2010 |
| WO | 99/40411 A1 | 8/1999 |
| WO | 03056327 A1 | 7/2003 |

OTHER PUBLICATIONS

EP Search Report in co-pending application EPA 16901813.2, dated Jul. 29, 2019.
S.N. Thennadll et al., "Empirical prepocessing methods and their impact on NIR calibrations: a simulation study", Journal of Chemometrics, 2005; 19: 77-89.
M. Rantalainen et al., "Kernel-based orthogonal projections to latent structures (K-OPLS)", Journal of Chemometrics, 2007; 21: 376-385.
Koji Asami, "Dielectric dispersion of erythrocyte ghosts", Physical Review E 73, 052903 (2006).
Koji Asami, "Design of a measurement cell for low-frequency dielectric spectroscopy of biological cell suspension", Meas. Sci. Technol. 22 (2011), pp. 1-7.
Koji Asami, "Dielectric spectroscopy reveals nanoholes in erythrocyte ghosts", Soft Matter, 2012, 8, 3250.
Mehmet Koseoglu et al., "Effects of hemolysis interferences on routine biochemistry parameters", Biochemia Medica 2011; 21 (1): 79-85.
Johan Trygg et al., "Orthogonal projections to latent structures (O-PLS)", J. Cemometrics 2002; 16: 119-128.
Max Bulosjo et al., "K-OPLS package: Kernel-based orthogonal projections to latent structures for prediction and interpretation in feature space", BMC Bioinformatics 2008, 9:106.
H. P. Schwan et al., "Dielectric Properties of the Membrane of Lysed Erythrocytes", Science, (1957); 125: pp. 985-986.
Bothwell, T. et al., "Electrical Properties of Plasma Membrane of Erythrocytes at Low Frequencies", Nature, (1956); 178: pp. 265-266.
KR office action in copending KR Appl. No. 10-2018-7032695 dated Jul. 13, 2020.
BR preliminary office action in copending BR Appl. No. 112018073186-2 dated Jul. 17, 2020.
CN office action in copending CN Appl. No. 201680085648.0, dated Sep. 11, 2020.

* cited by examiner

WHOLE BLOOD SO₂ SENSOR

BACKGROUND OF THE INVENTION

1. Field of the Invention

The present invention relates generally to an oxygen saturation sensor. Particularly, the present invention relates to an oxygen saturation sensor for use with whole blood.

2. Description of the Prior Art

Oxygen is carried in the blood attached to hemoglobin molecules. Oxygen saturation is a measure of how much oxygen the blood is carrying as a percentage of the maximum it could carry. One hemoglobin molecule can carry a maximum of four molecules of oxygen.

In other words, oxygen saturation is a term referring to the fraction of oxygen-saturated hemoglobin relative to total hemoglobin (unsaturated+saturated) in the blood. The human body requires and regulates a very precise and specific balance of oxygen in the blood. Normal arterial blood oxygen levels in humans are considered 95 to 100 percent. If the level is below 90 percent, it is considered low resulting in hypoxemia. Arterial blood oxygen levels below 80 percent may compromise organ function, such as the brain and heart, and continued low oxygen levels may lead to respiratory or cardiac arrest.

Oxygen saturation can be measured in different tissues. Venous oxygen saturation ($SvO_2$) is measured to see how much oxygen the body consumes. Under clinical treatment, a $SvO_2$ below 60% indicates that the body is in lack of oxygen, and ischemic diseases occur. This measurement is often used under treatment with a heart-lung machine (extracorporeal circulation), and can give the perfusionist an idea of how much flow the patient needs to stay healthy. Tissue oxygen saturation ($StO_2$) can be measured by near infrared spectroscopy. Although the measurements are still widely discussed, they give an idea of tissue oxygenation in various conditions. Peripheral capillary oxygen saturation ($SpO_2$) is an estimation of the oxygen saturation level usually measured with a pulse oximeter device.

The determination of hemoglobin oxygen saturation include in-vivo techniques by which a blood sample is withdrawn from a patient and sent to a laboratory for analysis. Pulse oximeters have been utilized for in-vivo determinations of blood hemoglobin oxygen saturation, but have not been used to provide information on hemoglobin concentration. Results obtain with these oximeters are often adversely affected by interference from venous blood, tissue, bone, ambient light, or patient motion.

Spectrophotographic techniques used to determine blood hemoglobin oxygen saturation may be subject to measurement error caused by the presence of dyshemoglobins in the blood sample. Dyshemoglobins, such as methemoglobin and carboxyhemoglobin, cannot transport oxygen but possess spectral absorbance. This spectral absorbance interferes with the absorbance of oxyhemoglobin, depending upon the wavelength of the incident light used.

It is typically believed by those of ordinary skill in the art that spectrophotometric measurements of blood hemoglobin oxygen saturation and hemoglobin concentration of non-hemolyzed whole blood are difficult and cannot achieve clinical accuracy due to the diffusive characteristics of whole blood.

SUMMARY OF THE INVENTION

In practice, typical COOx analyzers use lysed blood instead of whole blood because of the problems encountered with spectrometric analysis of whole blood. The measurement of lysed blood is relatively straightforward since the lysing process dissolves the red blood cells and turns the blood into an almost non-diffusing medium. The absorbance is measured with a simple collimated beam through the cuvette with little loss of light due to scattering. Because of the low loss of light due to scattering, a straightforward linear analysis may be used to find the oxygen saturation of the sample.

Measurement of oxygen saturation using a whole blood sample is very challenging due to the strong optical scattering of whole blood. These problems are primarily related to handling the increased light scattering level of whole blood as compared to lysed blood. This introduces light loss and nonlinear absorbance into the measurement.

The optical absorbance measurement of a diffuse sample such as whole blood presents a unique problem. The diffuse transmittance of the whole blood sample scrambles the initial spatial light distribution of the measurement system caused by the non-uniformity typical of light sources. Thus, the spatial light distribution of the "blank" scan can be quite different from the whole blood sample scan. Since optical detectors have response that varies spatially, the response can vary due to spatial distribution changes of the incident light, even if the overall intensity has not changed. An absorbance scan which is based on the ratio of the whole blood sample scan to the blank scan will have a significant absorbance component due to this non-uniformity of the light source in addition to the absorbance due to the sample alone. This results in a significant measurement error of the whole blood sample absorbance that is intolerable for oxygen saturation.

Current oxygen saturation sensors used in the spectrophotometric measurement on whole blood are typically a two wavelength (660 nm and 880 nm) reflective sensors. The two wavelength reflective sensors have slope and offset variation from sensor to sensor that is relatively large and represents typical behavior for these types of sensors. Further, the correlation r values between these types of sensors is also relatively poor.

It is an object of the present invention to provide an oxygen saturation sensor for use with whole blood that significantly decreases the unit-to-unit slope and offset variation. It is another object of the present invention to provide an oxygen saturation sensor for use with whole blood that significantly increases the correlation r value between sensors. It is a further object of the present invention to provide an oxygen saturation sensor for use with whole blood that cost about the same or less than the current two wavelength reflective sensors. It is still a further object of the present invention to improve the precision between SO2 sensors when measuring whole blood.

The present invention achieves these and other objectives by providing an oximeter sensor system that includes a light-emitting module providing light along an optical path, a light detector disposed in the optical path and a cuvette assembly disposed between the light-emitting module and the light detector.

In one embodiment of the present invention, the light-emitting module includes a light source group having a plurality of LEDs including at least a first visible light LED (a low wavelength band), a second visible light LED (a high wavelength band) and an infrared LED. An infrared filter is disposed in front of only the first and second visible light LEDs to filter out any infrared wavelength light from the visible light LEDs to avoid affecting the infrared wavelength band from the infrared LED. Many types of visible-band LEDs have a parasitic infrared emission that needs to be eliminated in this application. If a visible band LED does not have this parasitic infrared emission, then the filter is not necessary for that LED. The plurality of LEDs and the infrared filter are disposed in a light-source housing. The light-source housing has a base, one or more side walls and a light-emitting end. The light-source housing has a frustum shape with the light-source group disposed adjacent the base and facing the light-emitting end. The one or more side walls has a reflective coating, which reflects the light towards the light-emitting end creating an optical path.

In one embodiment of the present invention, an optical diffuser is disposed in the optical path between the light-source group and the cuvette assembly.

In another embodiment of the present invention, the light-emitting module includes a visible light filter disposed in front of the infrared LED.

In a further embodiment of the present invention, the first visible light LED has a low wavelength visible light range, the second visible light LED has a high wavelength visible light range, and the infrared LED has a wavelength range in the near infrared wavelength range.

In one embodiment of the present invention, the low wavelength visible light range has a wavelength range of no less than about 593 nm and no greater than about 620 nm, the high wavelength visible light range has a wavelength range of no less than about 634 nm and no greater than about 670 nm, and the infrared LED has a wavelength range of no less than 940 nm to about 960 nm with a nominal wavelength of 950 nm.

In one embodiment of the light source housing, the frustum shape is one of a cone shape, a pyramid shape or a multi-lateral shape.

In one embodiment of the present invention, the cuvette assembly has a cuvette module with a cuvette having a nominal path length of about 0.009 inches (0.23 mm).

In another embodiment, the oximeter sensor system has a computer processor module having at least a memory module, a processing module, a converter module, and a mathematical mapping function that maps absorbance values to percent oxygen saturation where the mapping function resides in either the memory module or the processing module and converts a digital signal received from the converter module into a measured value. The measured value is proportional to a percentage of oxygen saturation of a sample disposed in and being measured in the cuvette.

In one embodiment of the present invention, the mathematical mapping function is a kernel-based function.

In one embodiment of the present invention, the kernel-based function is a kernel-based orthogonal projections to latent structures function.

In one embodiment of the present invention, the mathematical mapping function maps absorbance values to percent oxygen saturation, which is generated from a plurality of absorbance values of samples having a known percent oxygen saturation for a predefined nominal path length of the cuvette.

In a further embodiment, the plurality of LEDs includes one or more additional visible light LEDs covering wavelength ranges different than the wavelength range of the first visible light LED and the second visible light LED. The additional visible light LEDs are used to provide total hemoglobin correction and/or removal of scattering effects and carboxyhemoglobin interference.

In another embodiment, there is disclosed an oximeter sensor for use in a system capable of measuring percent oxygen saturation in whole blood. The sensor includes a light-emitting module and a light detector. The light-emitting module has a light-source group having a plurality of LEDs, an optional infrared filter disposed in front of some of the plurality of LEDs that are visible light LEDs if the visible light LEDs have no infrared filtering capability, an optional visible light filter disposed in front of some of the plurality of LEDs that are infrared LEDs if the infrared LEDs have no visible light filtering capability, and a light source housing that has a base, one or more sidewalls and a light-emitting end where the light source housing has a frustum shape. The light source group is disposed adjacent the base and facing the light-emitting end. The one or more sidewalls has a reflective coating thereon.

In one embodiment of the oximeter sensor, the first visible light LED has a low wavelength visible light range, the second visible light LED has a high wavelength visible light range, and the infrared LED has a wavelength range in the near infrared wavelength range.

In one embodiment of the oximeter sensor, the low-wavelength visible light LED has a range of about 593-620 nm, the high-wavelength visible light LED has a range of about 643-669 nm and the wavelength for the infrared LED is about 950 nm.

In another embodiment, there is disclosed a light-emitting module for use in an SO2 sensor. The light-emitting module has a light source group having a plurality of LEDs consisting of a first visible light LED, a second visible light LED and an infrared LED adjacent the first visible light LED and the second visible light LED, and a light source housing having a base, one or more sidewalls and a light-emitting end where the light source housing has a frustum shape, where the light source group is disposed adjacent the base and facing the light-emitting end and where the one or more sidewalls has a reflective coating thereon.

In one embodiment, there is disclosed a method for measuring percent oxygen saturation in a whole blood sample using optical absorbance. The method includes measuring and recording a transmitted light intensity scan over a plurality of wavelengths in a measurement range by transmitting light through a cuvette module having an optical path with a known optical path length therethrough where the cuvette module is filled with a transparent fluid and where a transmitted light used for the transmitted light intensity scan originates from a light source group disposed in a light source housing having one or more sidewalls defining a frustum shape, the one or more sidewalls having a reflective coating thereon, and where the transmitted light through the cuvette module is received by a light detector. The method also includes measuring and recording a transmitted light intensity scan over the plurality of wavelengths of the measurement range by transmitting light through the cuvette module a second time where the cuvette module is filled with a whole blood sample, where each measuring and recording step of the transparent fluid and the whole blood sample includes diffusing the transmitted light before transmitting the light to and through the cuvette module and then determining a spectral absorbance at each wavelength of the plurality of wavelengths of the measurement range based on a ratio of the transmitted light intensity scan of the whole blood sample to the transmitted light intensity scan of the transparent fluid. The method further includes correlating the absorbance at each wavelength of the plurality of wavelengths of the measurement range to percent oxygen saturation values of the blood sample using a computational mapping function.

In another embodiment, the method includes selecting a computational mapping function that is a kernel-based mapping function. In a further embodiment, the mapping function is a kernel-based, orthogonal projection to latent structures function. The method further includes mapping the percent oxygen saturation values to respective known percent oxygen saturation values in blood.

DETAILED DESCRIPTION

Figure 1:
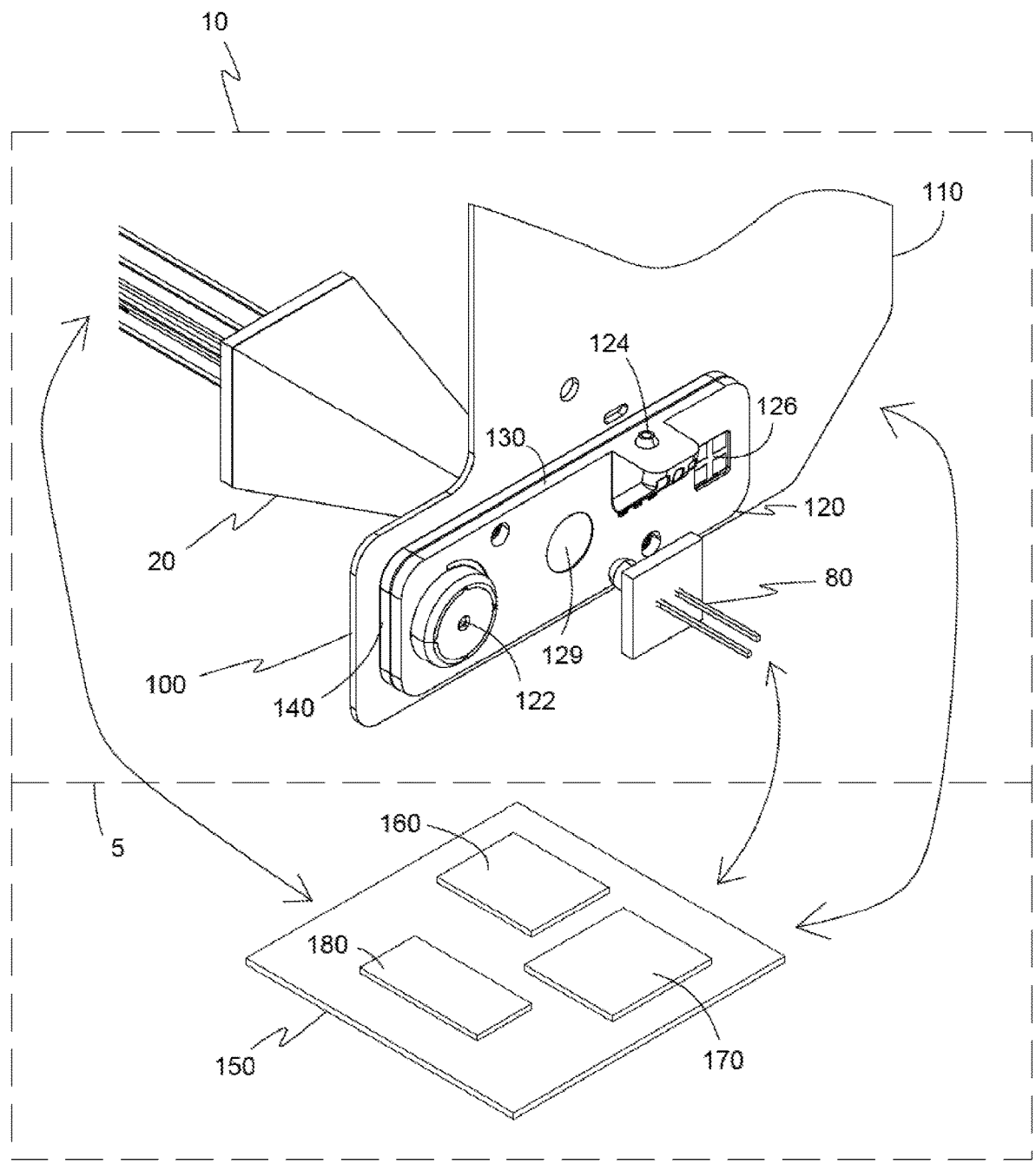
FIG. 1 is a front perspective view of one embodiment of the present invention showing the oximeter sensor, the cuvette, the light detector, and the processor module.

Embodiments of the present invention are illustrated in FIGS. 1-12. FIG. 1 shows one embodiment of an oximeter sensor subsystem 10. Sensor subsystem 10 includes a light-emitting module 20, a light detector 80 and a cuvette assembly 100 positioned between light-emitting module 20 and light detector 80. Sensor subsystem 10 may optionally include a processor module 150 or processor module 150 may optionally be included in an electronics circuit of a diagnostic system in which the oximeter sensor subsystem 10 is a part. Line 5 is included to signify that the processor module 150 may or may not be part of the oximeter sensor subsystem 10. Processor module 150 includes, but is not limited to a microprocessor module 160 and a memory module 170. Optionally, the processor module 150 may also include a converter module 180 or converter module 180 may be external to the oximeter sensor subsystem 10. Oximeter sensor subsystem 10 is used to measure the oxygen saturation ($SO_2$) of whole blood using optical absorbance.

Figure 2:
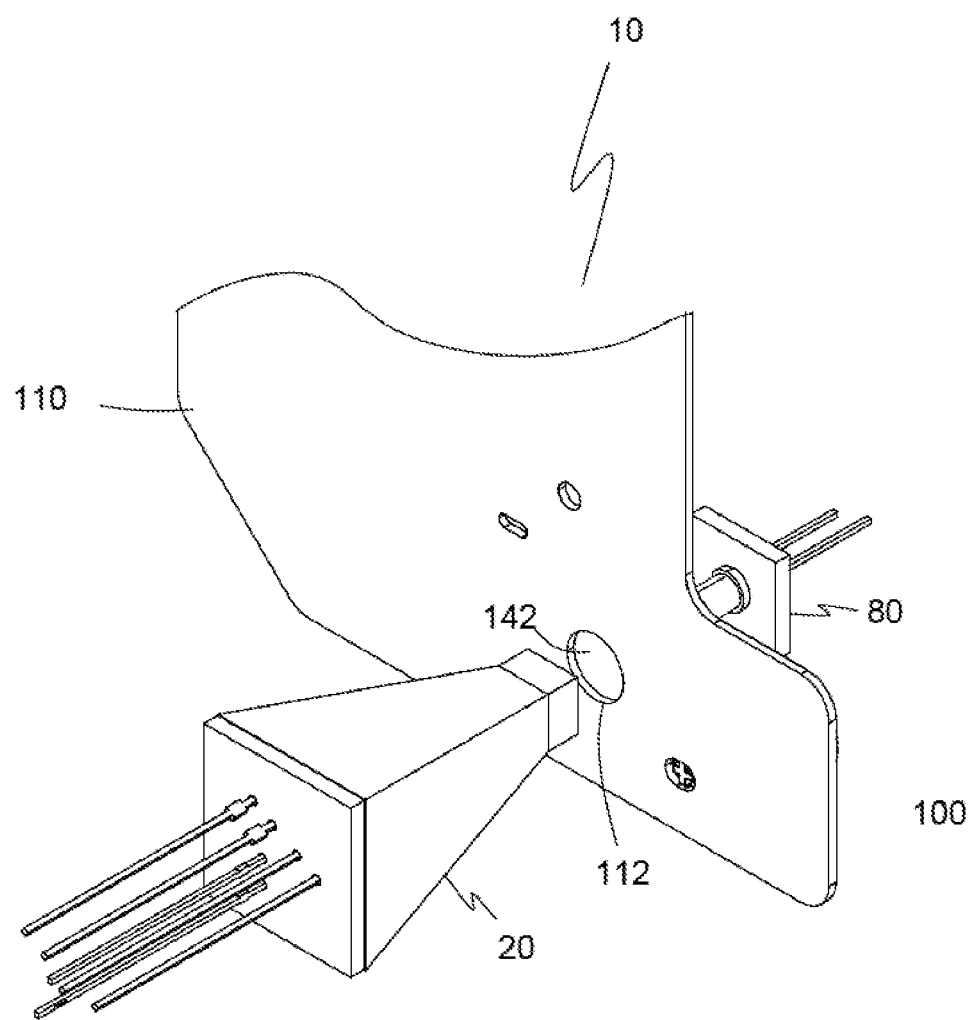
FIG. 2 is a rear perspective view of the embodiment in FIG. 1.

FIGS. 1 and 2 illustrate front and rear perspective views of one embodiment of the cuvette assembly 100. Cuvette assembly 100 includes a cuvette substrate 110 and a cuvette module 120. Cuvette substrate 110 provides a support for securing the cuvette assembly 100 within the oximeter sensor subsystem 10 and includes a cuvette light path opening 112 that is disposed within optical path 21 and is aligned with the light beam emitted from light-emitting module 20. Cuvette module 120 includes a cuvette first portion 130 having a sample receiving recess 135 (not shown), a sample inlet port 122, a sample outlet port 124, an electronic chip assembly 126, and a first cuvette window 129, and a cuvette second portion 140 having a second cuvette window 142 opposite and aligned with the first cuvette window 129 where the first and second cuvette windows 129, 142 are aligned with and disposed within optical path 21. Cuvette first portion 130 and cuvette second portion 140 are bonded to each with or without a gasket disposed between cuvette first and second portions 130, 140. Bonding may be achieved using adhesives, ultrasonic techniques, solvent based techniques, etc., all as is well known in the art. When assembled, cuvette first portion 130 and cuvette second portion 140 form a sample receiving chamber 102 (not shown) that fluidly communicates with sample inlet and outlet ports 122, 124. The distance between first and second cuvette windows 129, 142 of sample receiving chamber 102 define a cuvette optical path length, which is accurately measured and stored within electronic chip assembly 126 for later retrieval by processor module 150. A typical optical path length used in this embodiment of the present invention is 0.009 inches (0.23 mm).

Figure 3:
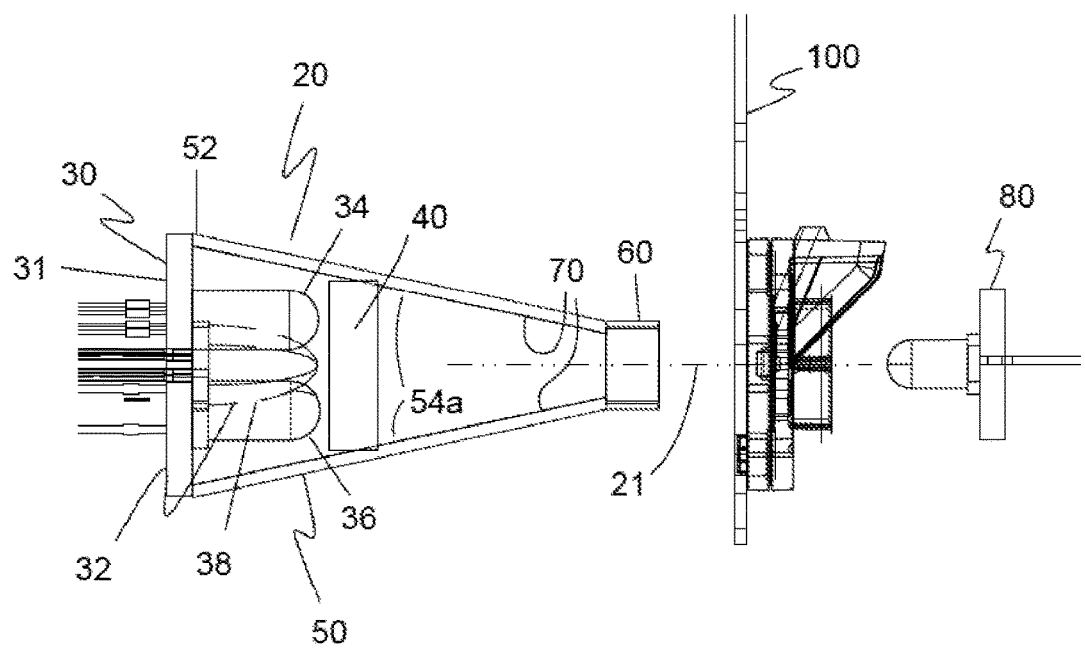
FIG. 3 is a side view of the embodiment in FIG. 1 showing a cross-sectional view of the oximeter sensor.

FIG. 3 illustrates a side view of oximeter sensor subsystem 10. In this view, a cross-section of light-emitting module 20 shows the various components that make up light-emitting module 20. Light-emitting module 20 has a light source group 30 and a light-source housing 50 that has a frustum shape with a light-emitting end 60 and a base 52. Light source group 30 includes a plurality of LEDs 32. More particularly in this embodiment, the plurality of LEDs 32 includes 3 LEDs, two visible light LEDs 34, 36 and an infrared LED 38. Visible light LED 34 is a low-wavelength visible band LED ranging from about 593 nm to about 620 nm. One example of a usable LED for the low-wavelength visible band is a LED part number Vishay TLCO5100 and available from Vishay Intertechnology, Inc., Malvern, Pa. Visible light LED 36 is a high-wavelength visible band LED ranging from about 634 nm to about 669 nm. It is noted that LEDs in the 660 nm range do not have a specified wavelength range but typically report a range of +/−15 nm. One example of a usable LED for the high-wavelength visible band is LED part number Kingbright WP1503 and available from Kingbright, City of Industry, Calif. Infrared LED 38 has a wavelength range of about 940-960 nm with a nominal wavelength of 950 nm. A wide, near infrared wavelength range is not required since the sensitivity of SO2 measurements in the infrared range of about 950 nm are much less sensitive to wavelength due to the flatness of the blood absorbance spectrum in that range. Typical prior art oxygen saturation sensors use two wavelengths of light for measurement purposes with some new types using more that the conventional two wavelengths to add measurement of additional parameters in addition to % SO2. The present invention uses three wavelengths, not to measure other blood parameters in addition to % SO2, but to increase % SO2 accuracy such as to provide total hemoglobin correction and/or orthogonal component removal (scattering effects and carboxy-hemoglobin interference) rather than for reporting additional analyte parameters.

Light-source housing 50 has one or more sidewalls 54 with an inside surface 54a upon which is disposed a reflective coating 70. Reflective coating 70 may be painted on or sprayed on or simply a thin layer of a reflective metal foil positioned against and/or adhered to the one or more sidewalls 54. It is noted that the frustum shape of light-source housing 50 may be conical or pyramidal or have any number of sidewalls 54 (i.e. multi-lateral) assembled together making up the frustum shape. Light-source group 30 has a plurality of LEDs 32 supported by a light-source substrate 31 where the light-source housing 50 directs the light from the plurality of LEDs 32 out of light-emitting end 60, which is aligned with first and second cuvette windows 129, 142 of cuvette assembly 100. On the opposite side of cuvette assembly 100 from light-emitting module 20 is light detector 80. Light detector 80 is aligned with first and second cuvette windows 129, 142 of cuvette assembly 100 so that it receives the light from light-emitting module 20 transmitted through cuvette module 120 of cuvette assembly 100. It is important to note, but not a requirement, that the frustum shape of the light-emitting module 20 allows the use of a single photodiode as light detector 80.

Figure 4:
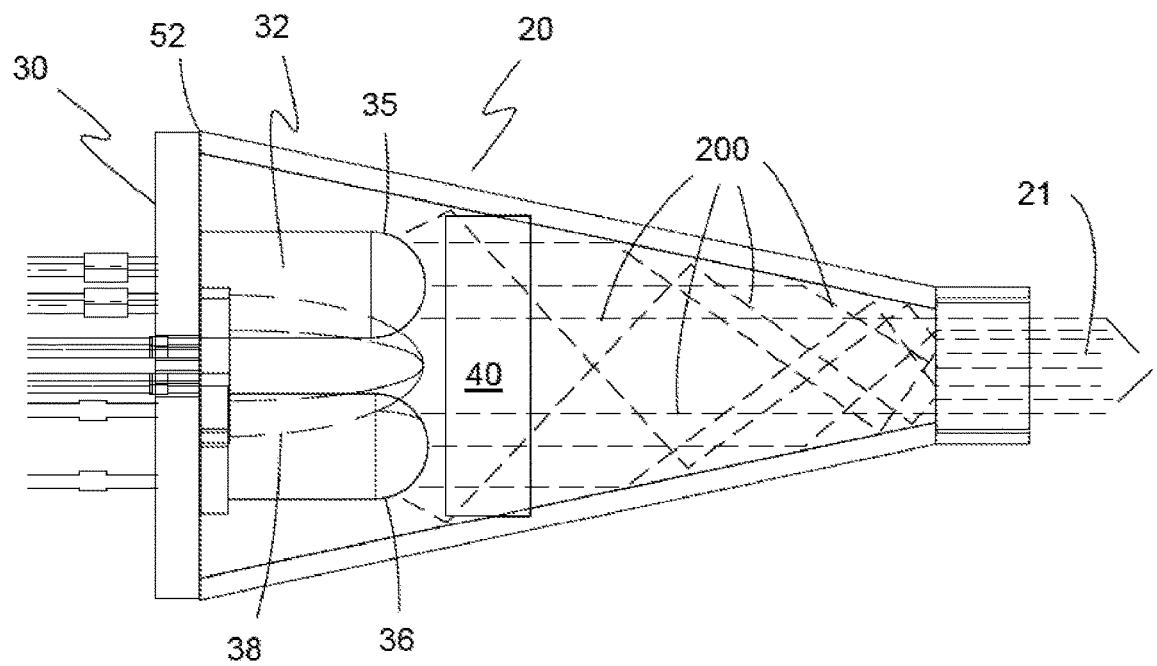
FIG. 4 is an enlarged side view of the oximeter sensor shown in FIG. 3 and illustrating the light rays from the plurality of LEDs forming the optical path.

FIG. 4 is an enlarged, cross-sectional view of light-emitting module 20. FIG. 4 shows a representation of a plurality of light rays 200 from the plurality of LEDs 32. Reflective coating 70 and the frustum shape of light-source housing 50 concentrates the plurality of light rays 200 to emit from light-emitting end 60, which is smaller than housing base 52 and light-source group 30. The shape of light-source housing coupled with reflective coating 70 provides the additional benefit of mixing and making uniform the spatial light distribution when transmitting light through a sample of whole blood.

Figure 5:
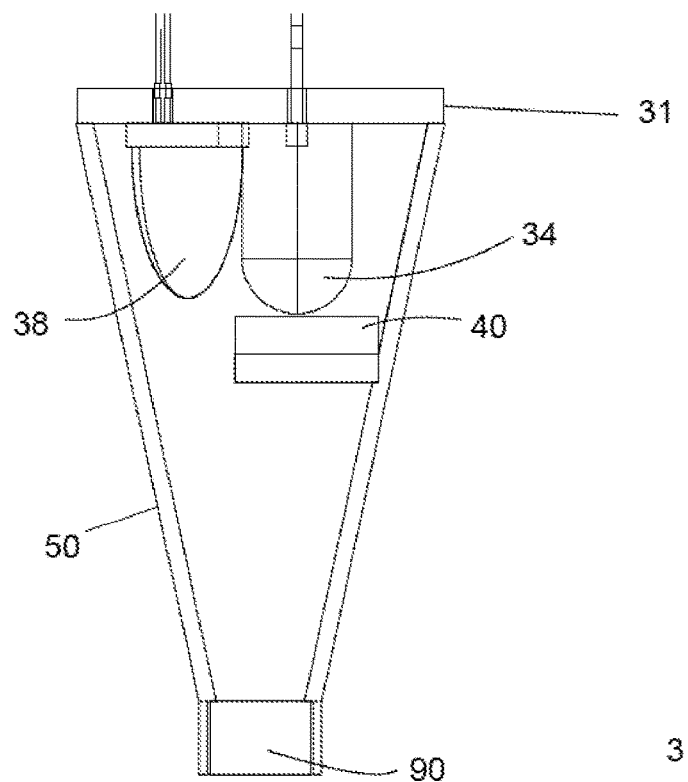
FIG. 5 is a top view of the oximeter sensor shown in FIG. 3.

FIG. 5 is an enlarged, top view of light-emitting module 20. As can be seen, infrared light filter 40 is positioned in front of first and second visible light LEDs 34, 36. Adjacent first and second visible light LEDs is an infrared light LED 38. Infrared light filter 40 prevents any infrared light emitted from first and second visible light LEDs 34, 36 from being transmitted to cuvette module 120 so than only the infrared light wavelengths emitted from infrared light LED 38 is transmitted through cuvette module 120. At, within or adjacent light-emitting end 60 of light-emitting module 20 is optical diffuser 90. Optical diffuser 90 acts to diffuse the light being emitted from light-emitting end 60 so that the light transmittance intensity is constant across the cross-sectional area of light-emitting end 60. One example of an acceptable optical diffuser 90 is opal diffusing glass with a thickness of about 3 mm (Edmund Optics part number 46166 is an example of such a glass).

Figure 6:
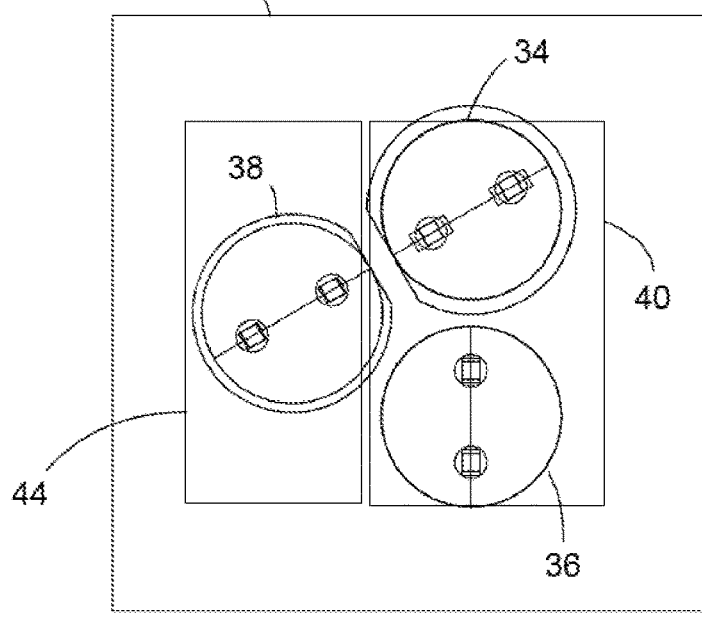
FIG. 6 is a cross-sectional view of the oximeter sensor of FIG. 3 showing the position of the LEDs, the infrared filter and optional visible light filter.

FIG. 6 is an end view of light-source group 30 with infrared filter 40. It can be seen that infrared filter 40 is positioned only in front of first visible light LED 34 and in front of second visible light LED 36. In one embodiment, infrared light LED 38 has a cover that acts as a visible light filter so no visible light from infrared light LED 38 is emitted causing incorrect correlations of first and second visible light LEDs 34, 36. In other embodiments when an infrared light LED 38 is used whose cover does not act as a visible light filter, a separate visible light filter 44 is included in light-emitting module 20 and positioned in front of infrared light LED 38, which is shown in FIG. 6 as an optional visible light filter 44 adjacent visible light filter 40. Filter 44 is typically made of an acrylic material such as ACRYLITE® GP part number 1146-0 (IRT) from GYRO Industries. Filter 40 may be made of Schott part number KG5 glass with a thickness of 3 mm.

Figure 7:
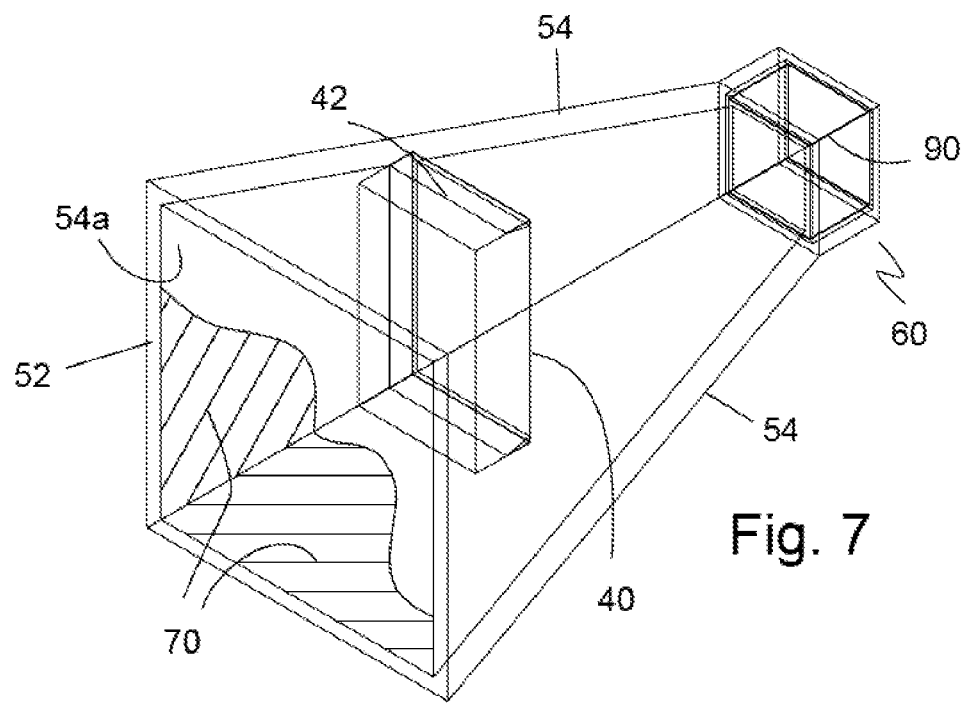
FIG. 7 is a rear perspective view of the light source housing of the oximeter sensor in FIG. 3 showing the infrared filter and the optical diffuser.

Turning now to FIG. 7, there is illustrated a perspective, transparent view of light-source housing 50 with visible light filter 40 and optical diffuser 90. Visible light filter 40 is secured to a filter support 42 positioned a predefined distance from housing base 52. Filter support 42 is located so that visible light filter 40 is directly in front of first and second visible light LEDs 34, 36. In this embodiment, optical diffuser 90 is positioned within a housing end recess 62 at light-emitting end 60. Inside surface 54a of sides 54 has disposed thereon reflective coating 70.

Figure 8:
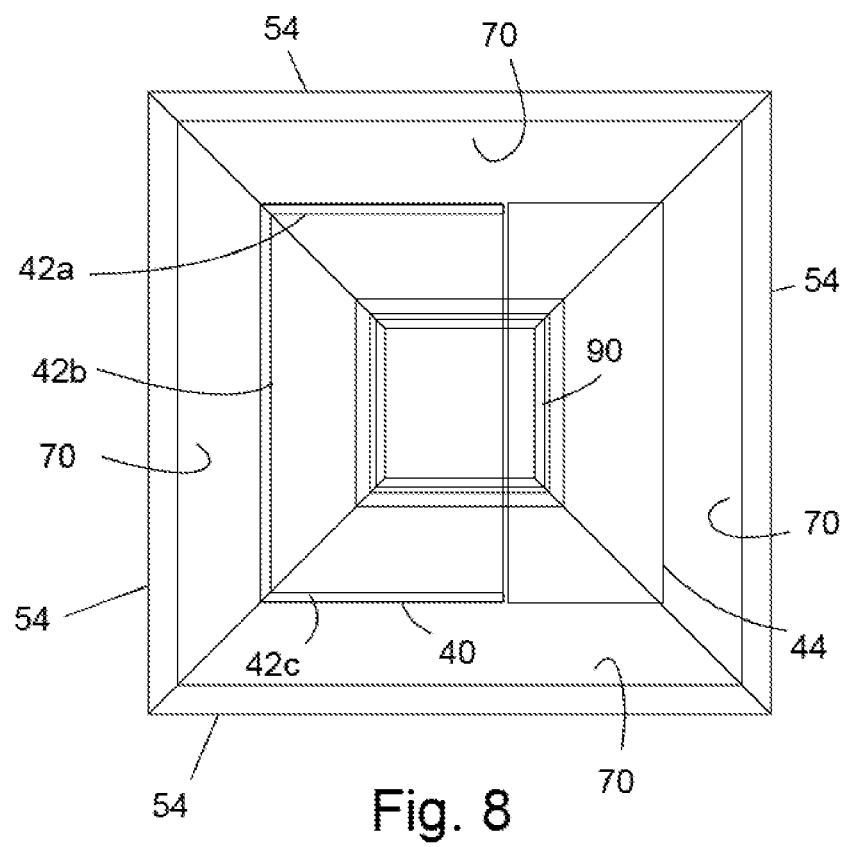
FIG. 8 is a rear view of the light source housing shown in FIG. 7.

FIG. 8 is a plan view of light-source housing 50 of FIG. 7 from base 52. In this embodiment, filter support 42 is illustrated as having support portions 42a, 42b, 42c positioned against inside surface 54a of sides 54. Visible light filter 40 is attached to support portions 42a, 42b, 42c along corresponding sides of visible light filter 40.

Figure 9:
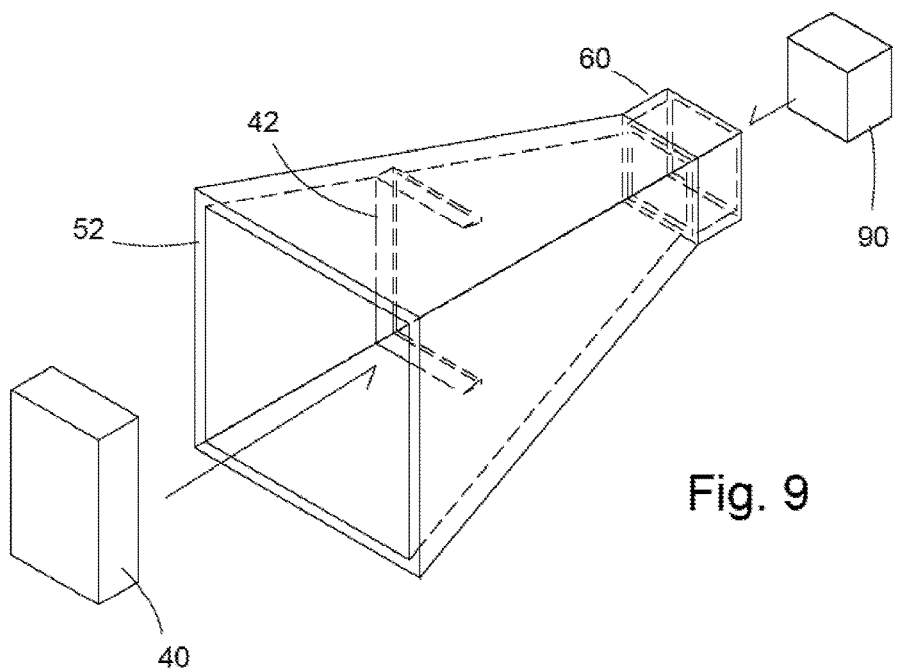
FIG. 9 is an exploded view of the light source housing shown in FIG. 7.

FIG. 9 is a perspective, exploded view of light-source housing 50 shown in FIG. 7. Visible light filter 40 is positioned against and supported by filter support 42 through housing base 52. Any suitable adhesive may be used to secure visible light filter 40 to filter support 42. Also in this embodiment, optical diffuser 90 is disposed into housing end recess 62 of light-emitting end 60. As described for visible light filter 40, any suitable adhesive may be used to secure optical diffuser 90 to light-emitting end 60.

Figure 10:
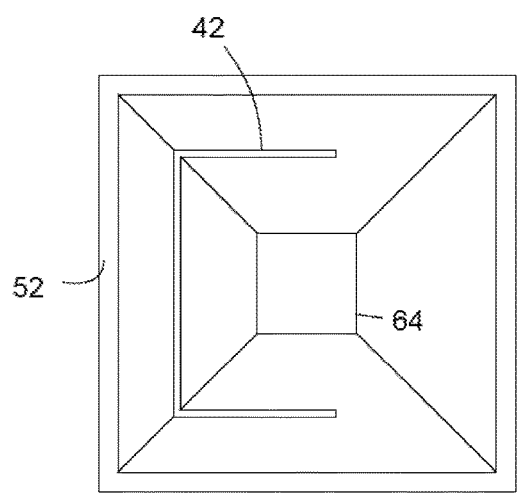
FIG. 10 is a rear view of the light source housing shown in FIG. 10.
Figure 11:
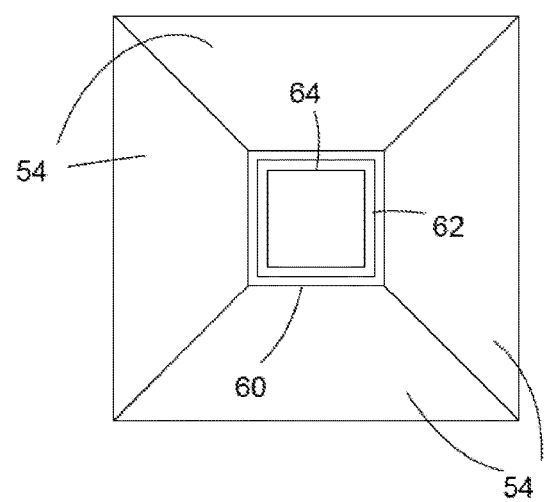
FIG. 11 is a front view of the light source housing shown in FIG. 10.

FIG. 10 is plan view of only light-source housing 50 shown in FIG. 9. Sidewalls 54 taper from base 52 toward a light-exit port 64 at light-emitting end 60. FIG. 11 is an end plan view of light-source housing 50 shown in FIG. 9. From this viewpoint, there is show housing end recess 62, which is larger than light-exit port 64 but smaller than light-emitting end 60. Housing recess 62 is configured to receive optical diffuser 90 therein. It should be understood that optical diffuser 90 does not have to be disposed within light-emitting end 60 but may be supported by a support structure separate from light-emitting housing 50 so long as optical diffuser 90 is positioned within the optical path 21 between light-emitting housing 50 and cuvette module 120 and that the size of optical diffuser 90 is sufficient to prevent any light from light-emitting module 20 impinging on first and second cuvette windows 129, 142 of cuvette module 120 without passing through optical diffuser 90.

Learning Data:

A data set of about 40 blood samples from approximately 10 different individuals was developed. A tonometer was used to manipulate the oxygen level in each blood sample. Plasma was removed from or added to samples to change the total hemoglobin (tHb) level. The blood samples were manipulated to cover a range of tHB, carboxyhemoglobin (COHb), deoxyhemoglobin (HHb), and oxyhemoglobin (O2Hb) values. Samples with COHb greater than 15% or with % SO2 less than 20% were not included in the model development data. The samples were measured with the SO2 sensor as described. The cuvettes used had a path length of 0.009" (0.23 mm). This data set has been turned into a Matlab cell array file for use with Matlab scripts. The SO2 level of the blood samples were also measured on a reference lysing pHOx Ultra analyzer (Nova Biomedical) equipped with COOx analyzer and analysis software.

Prediction Model:

The next step in the calculation is to create a prediction model. Using an initial calibration data set, the calibration sequence of a machine learning algorithm establishes a relationship between a matrix of known sample characteristics (the Y matrix) and a matrix of measured percent oxygen saturation values at several absorbance values and potentially other measured values (the X matrix). The absorbance at each wavelength may be considered as independent values and used separately as well as together. Once this relationship is established, it is used by analyzers to predict the unknown Y values from new measurements of X on samples. The calibration set Y matrix is built up as follows from the known values of the calibration sample set of n blood samples:

$$Y = \begin{bmatrix} \%\ SO2_1 & tHb_1 \\ \%\ SO2_2 & tHb_2 \\ \vdots & \vdots \\ \%\ SO2_n & tHb_n \end{bmatrix}$$

where % SO2 is the percentage of oxygen saturation, and tHb is the total hemoglobin for a particular sample n.

Although the tHb may be left out without adversely affecting the usefulness of the present invention, it is noted that total hemoglobin was added as a predictive component in case it was needed to correct the % SO2 value.

The rows of the X matrix are structured as follows:

$$X_n = \left[ \frac{A_{n,\lambda_1}}{A_{n,950nm}}, \frac{A_{n,\lambda_2}}{A_{n,950nm}}, A_{n,950nm} \right] \text{ and:}$$

$$X = \begin{bmatrix} X_1 \\ \vdots \\ X_n \end{bmatrix}$$

where: $A_{n,\lambda_1}$ and $A_{n,\lambda_2}$ represent the absorbance values for the visible light LEDs, respectively for a particular sample n.

$A_{n,950\ nm}$ represents the absorbance value for the infrared LED for a particular sample n.

Using an initial calibration data set, the calibration sequence of a machine learning algorithm establishes a relationship between a matrix of known sample characteristics (the Y matrix) and a matrix of measured absorbance values at several wavelengths and potentially other measured values based on absorbance versus wavelength (the X matrix). Once this relationship is established, it is used by the analyzer to predict the unknown Y values from new measurements of X on whole blood samples.

Once these matrices are formed, they are used as the calibration set and the mapping function is computed according to the procedures particular to the machine learning algorithm chosen.

Conventional partial least squares, linear regression, linear algebra, neural networks, multivariate adaptive regression splines, kernel-based orthogonal projection to latent structures, or other machine learning mathematics is used with results obtained from the calibration set of data to determine the empirical relationship (or mapping function) between the absorbance values and the percent oxygen saturation. Typically, a mathematics package is used to generate the results where the package generally has options to select one of the machine learning mathematics known to those skilled in the art. Various mathematics packages exist and include, but are not limited to, Matlab by MatWorks of Natick, Mass., "R" by R Project for Statistical Computing available over the Internet at www.r-project.org, Python from Python Software Foundation and available over the Internet at www.python.org in combination with Orange data mining software from Orange Bioinformatics available over the Internet at orange.biolab.si, to name a few.

It will be shown that the method of Kernel-Based Orthogonal Projection to Latent Structures (KOPLS) may be used as one type of machine learning algorithm to generate the mapping function. An explanation and description of KOPLS is best exemplified by the following references: Johan Trygg and Svante Wold. "*Orthogonal projections to latent structures (O-PLS)*." J. Chemometrics 2002; 16: 119-128; Mattias Rantalainen et al. "*Kernel-based orthogonal projections to latent structures (K-OPLS)*." J. Chemometrics 2007; 21: 376-385; and Max Bylesjö et al. "*K-OPLS package: Kernel-based orthogonal projections to latent structures for prediction and interpretation in feature space*." BMC Bioinformatics 2008, 9:106, which references are incorporated herein by reference. The kernel-based mathematics is useful in handling non-linear behavior in systems by using a kernel function to map the original data to a higher order space. Although any of the previously described machine learning mathematics may be used to enable one of ordinary skill in the art to practice the present invention, KOPLS has an additional advantage over other calculations such as, for example, conventional partial least squares because it can not only establish a relationship between quantified variations and analyte values to be determined, but can also remove unquantitated yet consistently present variation in the original data. These unquantitated variations might be due to sample characteristics, analyzer baseline variations, drifts, etc.

Using an initial training data set, the KOPLS model establishes a relationship (mapping function) between the matrix of known sample characteristics (the Y matrix), and a matrix of measured absorbance values at several wavelengths and potentially other measured values (the x matrix) as processed through a kernel function as specified by the KOPLS method. The value of the absorbance at each wavelength may be considered as independent values and used separately as well as together. Once the KOPLS coefficients of this relationship are established, they are used with the kernel function by analyzers to predict the unknown Y values from new measurements of X on samples.

The kernel function used in this example is a simple linear kernel function described in the Mattias Rantalainen et al. reference listed above and represented by the following equation:

$$\kappa(X,X) = \langle X,X \rangle$$

where the matrix of measured values X is put into the kernel function and subjected to further processing as specified in the cited KOPLS references above (incorporated by reference) for creating the KOPLS training coefficients.

Once the set of training coefficients, or mapping function, is established, it is used to predict the % $SO_2$ value of a blood sample from future measurements. A single-row X matrix is created from the new measurements, then the value from this single-row X matrix is put through the kernel and mapping functions to produce the % $SO_2$ value according to the procedures necessary for the mapping function used according to the KOPLS procedures described in detail in the KOPLS references disclosed previously.

The data collected from the blood samples described above were put through the KOPLS method in a cross-validation process. Cross-validation is a process for using a data set to test a method. Several data rows are set aside and the rest are used to create a mapping function. The set-aside values are then used as "new" measurements and their Y matrix values calculated. This process is repeated by setting aside other measured values and computing another mapping function. By plotting the known values of the blood data vs. the calculated, the effectiveness of the method may be ascertained by inspecting the plot. The X-data array was constructed from terms created from the measured absorbance at two visible wavelength bands and one infrared wavelength. A low-wavelength visible band used LEDs ranging from 593-620 nm, a high-wavelength visible band used LEDs ranging from 634-669 nm, and an infrared wavelength used was a nominal 950 nm.

Because the gain and offset of sensors made with different sets of LEDs was found to vary with particular visible band LED wavelength, a means to correct the gain and offset of each sensor based on the particular wavelengths of the individual LEDs was developed. The cross-validation correlation line for each sensor has a separate gain and offset for each sensor. The coefficients of a two-axis polynomial function relating the mean LED low-wavelength visible band ($\lambda_1$) and the mean LED high-wavelength visible band ($\lambda_2$) to the gain and offset correction to be applied to each different sensor was fitted to all of the sensor gain and offset vs. wavelength data. The polynomial-fit procedure may be implemented using one of many standard math software packages such as Matlab, Python, R, or computer languages such as FORTAN or C. The SO2 predictions were gain and offset corrected using these polynomial coefficients (Equations 1 and 2 below).

$$\text{Gain} = a_G + b_{G1}\lambda_1 + b_{G2}\lambda_2 + c_G\lambda_1\lambda_2 + d_{G1}\lambda_1^2 + d_{G2}\lambda_2^2 \quad \text{Eq. 1}$$

$$\text{Offset} = a_O + b_{O1}\lambda_1 + b_{O2}\lambda_2 + c_O\lambda_1\lambda_2 + d_{O1}\lambda_1^2 + d_{O2}\lambda_2^2 \quad \text{Eq. 2}$$

The use of the gain and offset correction provide precision between sensors to within a 1% standard deviation. The structure of the SO2 sensor described previously (i.e. the frustum shape of the light source housing), reduces scatter in the data between the sensors to the point that it was possible to discern an additional offset dependency on the tHb level in the sample. Consequently, a tHb offset was determined from the results, which was added to the predicted % SO2 value. Equation 3 below was used to calculate this offset:

$$-0.5714 \times Y_{tHb} + 7.856 \quad \text{Eq. 3}$$

where the $Y_{tHb}$ value (not to be confused with the Y matrix) is the tHb value predicted from the KOPLS model.

Figure 12:
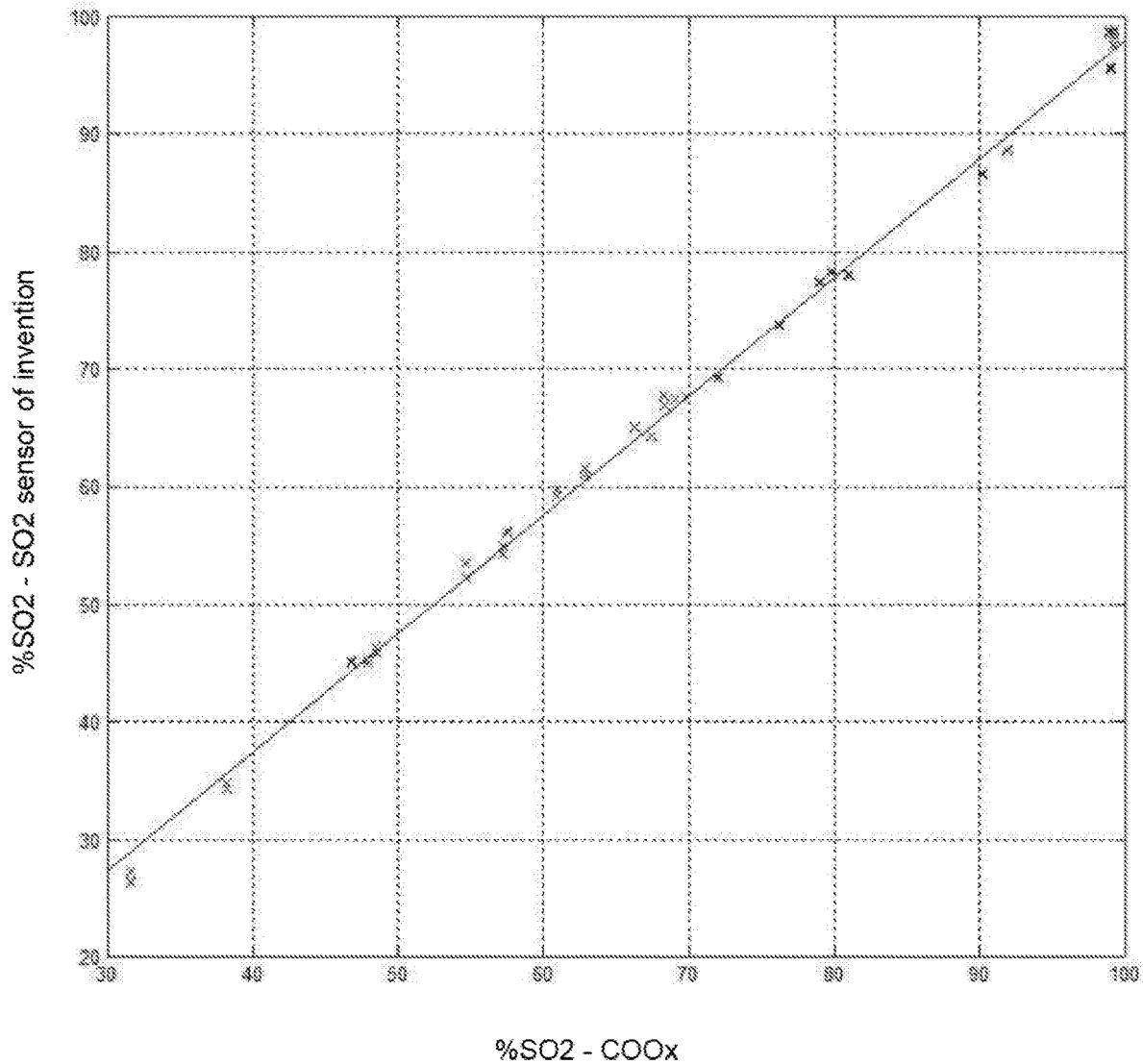
FIG. 12 is a graphical illustration of a correlation plot and data for a sensor having the frustum-shaped light source housing shown in FIGS. 2-5.

FIG. 12 illustrates a correlation plot and data for a sensor having the frustum shape of the light source housing. As can be seen, there is very little scatter of the data points; meaning that the data points are very close to the slope line.

It is important to note that typical SO2 sensors such as those used on Nova Biomedical's CCX and pHOx Ultra analyzers have considerable slope and offset variation between sensors. The 95% confidence limits for three tested pHOx Ultra sensors are in the range of 4.8–7.2% SO2.

Precision runs for the SO2 sensor of the present invention were also performed on twenty consecutive samples at three different % SO2 levels with a common optical path. Table 1 illustrates the average precision for these twenty consecutive samples.

TABLE 1

Precision runs for SO2 Sensor

| | % SO2 value | | |
|---|---|---|---|
| | % SO2 = 94% | % SO2 = 84% | % SO2 = 30% |
| Precision | 0.16% | 0.29% | 0.69% |

The 95% confidence limits for the SO2 sensor of the present invention is 1.1% SO2, which is considerably reduced from the 4.8-7.2% SO2 levels for the pHOx Ultra SO2 sensors.

The SO2 sensor of the present invention lists several advantages over conventional SO2 sensors. The present invention significantly decreases the unit-to-unit slope and offset variation of the SO2 sensor. The present invention also provides a significant increase in the correlation r value of the SO2 sensor. In addition, the present invention provides significantly increased precision in the measurement of % SO2 between sensors.

The present invention also includes a method of measuring percent oxygen saturation in a whole blood sample. The method includes measuring an optical absorbance of a whole blood sample at a plurality of visible light wavelengths and at an infrared wavelength using an oximeter sensor system 10 that includes a light-emitting module 20. The method involves guiding light at the plurality of wavelengths from a plurality of LEDs 32 located at a base 52 of a housing 50 having a frustum shape out of the housing 50 at a light-emitting end 60 along an optical path 21 directed to a cuvette module 120 containing a sample of the whole blood. The light is directed out of cuvette module 120 to a light detector 80. The method further includes calculating an absorbance value for each of the plurality of visible light wavelengths and at the infrared wavelength and subjecting each absorbance value calculated in the previous step to a mapping kernel-based function that maps absorbance values to percent oxygen saturation.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An oximeter sensor system for use in a whole-blood COOx analyzer to measure oxygen saturation of a whole-blood sample, the sensor comprising:
   a light-emitting module comprising:
   a light source group having a plurality of LEDs including at least a first visible light LED having a low wavelength visible light range, a second visible light LED having a high wavelength visible light range and an infrared LED having a wavelength range in the near infrared wavelength range, wherein the low wavelength visible light range has a wavelength range of no less than about 593 nm and no greater than about 620 nm, the high wavelength visible light range has a wavelength range of no less than about 634 nm and no greater than about 669 nm, and the infrared LED has a wavelength range of no less than 940 nm;
   a light source housing having a frustum shape with a base, one or more sidewalls and a light-emitting end opposite the base of the frustum shape, wherein measuring of the blood sample further includes discerning an additional offset dependency on total hemoglobin (tHb) level in the sample and correcting therefor by providing the base has a size being larger than a size of the light-emitting end, wherein the light source the light source group is disposed adjacent the base of the frustum shape and facing the light-emitting end, and wherein the one or more sidewalls has a reflective coating thereon;
   a light detector disposed opposite to, spaced from and facing the light-emitting end of the light source housing; and
   a cuvette assembly disposed between the light-emitting end of the light source housing and the light detector whereby the cuvette assembly is configured to receive the whole-blood sample.

2. The sensor system of claim 1 further comprising a diffuser disposed between the light-source group and the cuvette.

3. The sensor system of claim 1 further comprising a visible-light blocking filter disposed in front of the infrared LED when the infrared LED does not have a cover that acts as a visible light filter.

4. The sensor system of claim 1 further comprising an infrared-light blocking filter disposed in front of one or both visible light LEDs.

5. The sensor system of claim 1 wherein the frustum shape of the light source housing is one of a cone shape, a pyramid shape or a multi-lateral shape.

6. The sensor system of claim 1 wherein the cuvette has a nominal path length of about 0.009 inches (0.23 mm).

7. The sensor system of claim 1 wherein the plurality of LEDs includes one or more additional visible light LEDs covering wavelength ranges different than the wavelength range of first visible light LED and second visible light LED wherein the additional visible light LEDs are used to provide total hemoglobin correction and/or removal of scattering effects and carboxyhemoglobin interference.

8. A light-emitting module for an oximeter sensor for use in a whole-blood COOx analyzer to measure percent oxygen saturation of a whole blood sample, the module comprising:
a light source group having a plurality of LEDs consisting of a first visible light LED having a low wavelength visible light range, a second visible light LED having a high wavelength visible light range and an infrared LED having a wavelength range in the near infrared wavelength range, the infrared LED adjacent the first visible light LED and the second visible light LED, wherein the low wavelength visible light range has a wavelength range of no less than about 593 nm and no greater than about 620 nm, the high wavelength visible light range has a wavelength range of no less than about 634 nm and no greater than about 669 nm, and the infrared LED has a wavelength range of no less than 940 nm; and
a light source housing having a frustum shape with a base, one or more sidewalls and a light-emitting end, wherein measuring of the blood sample further includes discerning an additional offset dependency on total hemoglobin (tHb) level in the sample and correcting therefor by providing the base of the light housing with a diameter larger than a diameter of the light-emitting end, wherein the light source group is disposed adjacent the base of the frustum shape and facing the light-emitting end, and wherein the one or more sidewalls has a reflective coating thereon.

9. The module of claim 8 further comprising a visible-light blocking filter disposed in front of the infrared LED when the infrared LED does not have a cover that acts as a visible light filter.

10. The sensor of claim 8 further comprising an infrared-light blocking filter disposed in front of one or both visible LEDs.

11. The sensor system of claim 8 wherein the frustum shape of the light source housing is selected from the group consisting of a cone shape, a pyramidal shape and a multi-lateral shape.

12. A method of measuring percent oxygen saturation in a whole blood sample, the method comprising:
a. measuring an optical absorbance of a blood sample at a plurality of visible light wavelengths and at an infrared wavelength using an oximeter sensor system comprising:
a light source group incorporating a plurality of LEDs mounted within a light source housing having a frustum shape with a base wherein the plurality of LEDs includes a first visible light LED having a low wavelength visible light range, a second visible light LED having a high wavelength visible light range and an infrared LED having a wavelength range in the near infrared wavelength range, one or more sidewalls and a light-emitting end, wherein the light source group is disposed adjacent the base of the frustum shape and facing the open top, and wherein the one or more sidewalls has a reflective coating thereon;
a light detector disposed opposite to, spaced from and facing the light-emitting end of the light source housing; and
a cuvette module disposed between the light-emitting end of the light source housing and the light detector;
b. calculating an absorbance value for each of the plurality of visible light wavelengths and at the infrared wavelength; and
c. subjecting each absorbance value calculated in step b to a mapping function that maps absorbance values to percent oxygen saturation;
wherein the step of measuring the optical absorbance of the blood sample further includes discerning an additional offset dependency on total hemoglobin (tHb) level in the sample and correcting therefor by providing the base of the light housing with a diameter larger than a diameter of the light-emitting end.

13. The method of claim 12 wherein the step of determining the function that maps absorbance values to percent oxygen saturation further comprising:
measuring a plurality of absorbance values for a cuvette having predefined optical path length at a plurality of light wavelengths using a plurality of blood samples containing known but varying percentages of oxygen saturation; and
creating a calibration data set using a function that maps absorbance values to percent oxygen saturation to establish a relationship between a first Y matrix of known sample characteristics including percent oxygen saturation and a second X matrix of measured absorbance values at the plurality of predefined light wavelengths wherein the calibration data set and matrix relationship are used in computation of the function that maps absorbance values to percent oxygen saturation.

14. The method of claim 12 wherein the subjecting step further includes processing the electrical signal to spectral absorbance and then mapping the spectral absorbance to oxygen saturation values using a computational mapping function.

15. The method of claim 14 wherein the subjecting step includes using a kernel-based orthogonal projection to latent structures mapping function as the computational mapping function.

16. The method of claim 12 further comprising:
measuring and recording a transmitted light intensity scan over the plurality of wavelengths in a measurement range by transmitting light through the cuvette module wherein the cuvette module has an optical path with a known optical path length therethrough wherein the cuvette is filled with a transparent fluid and wherein a transmitted light used for the transmitted light intensity scan originates from the light source group wherein the transmitted light through the cuvette module is received by the light detector;

measuring and recording another transmitted light intensity scan over the plurality of wavelengths of the measurement range by transmitting light through the cuvette module a second time having the optical path with the known optical path length therethrough wherein the cuvette module is filled with a whole blood sample, wherein each measuring and recording step of the transparent fluid and the whole blood sample includes diffusing the transmitted light before transmitting the transmitted light through the cuvette module;

determining a spectral absorbance at each wavelength of the plurality of wavelengths of the measurement range based on a ratio of the transmitted light intensity scan of the whole blood sample to the transmitted light intensity scan of the transparent fluid; and correlating the absorbance at each wavelength of the plurality of wavelengths of the measurement range to percent oxygen saturation values of the blood sample using a computational mapping function.

17. The method of claim 16 further comprising selecting the first visible light LED having a wavelength range of no less than about 593 nm and no greater than about 620 nm, the second visible light LED having a wavelength range of no less than about 634 nm and no greater than about 669 nm, and the infrared LED having a wavelength range of no less than 940 nm.

18. The method of claim 16 wherein the correlating step further includes selecting a computational mapping function that is a kernel-based orthogonal projection to latent structures function.

19. The method of claim 16 wherein the correlating step includes mapping the percent oxygen saturation values to respective known percent oxygen saturation values in blood.

* * * * *